| United States Patent [19]
Taylor, Jr.

[11] 3,956,496
[45] May 11, 1976

[54] INHIBITION OF GASTRIC ACID SECRETION WITH 2-(TETRAHYDROFURYL)PERIMIDINE
[75] Inventor: Russell J. Taylor, Jr., Palmyra, N.J.
[73] Assignee: McNeil Laboratories, Incorporated, Fort Washington, Pa.
[22] Filed: Dec. 12, 1974
[21] Appl. No.: 532,121

Related U.S. Application Data
[63] Continuation-in-part of Ser. No. 417,705, Nov. 20, 1973, abandoned.

[52] U.S. Cl. .............................................. 424/251
[51] Int. Cl.² ...................................... A61K 31/505
[58] Field of Search ..................... 424/251; 417/705

[56] References Cited
UNITED STATES PATENTS
3,502,647  3/1970  Paragamian .................... 260/209

OTHER PUBLICATIONS
Curren Therapy (1963) pp. 256–257.
Text. of Org. Med. and Pharm. Chem., pp. 346–348, (1962) 4th Ed., J. B. Lippincott Co., Phila., Montreal.

Primary Examiner—Frederick E. Waddell

[57] ABSTRACT
The use of 2-(tetrahydrofuryl)perimidine as an inhibitor of gastric acid secretion.

2 Claims, No Drawings

INHIBITION OF GASTRIC ACID SECRETION WITH 2-(TETRAHYDROFURYL)PERIMIDINE

REFERENCE TO PRIOR APPLICATION

This application is a continuation-in-part- of a copending Application Ser. No. 417,705, filed Nov. 20, 1973, now abandoned.

DESCRIPTION OF THE INVENTION

This invention relates to the use of the known compound, 2(tetrahydrofuryl)perimidine, as an aid in the inhibition of gastric acid secretion in man or animals. The compound, which has the structural formula:

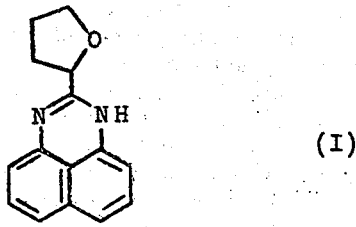

(I)

is described in U.S. Pat. No. 3,502,647 (see Example XIX). The pharmaceutically acceptable acid addition salts of (I) are also included within the scope of this invention.

2-(Tetrahydrofuryl)perimidine and salts thereof are useful antisecretory agents as shown, for example, by their ability to inhibit gastric acid secretion in standard laboratory animal tests. For example, antisecretory activity is observed in the 3-hour pyloricligated rat test at intraperitoneal (i.p.) or oral dose levels of about 10–100 mg/kg body weight.

The test procedure is a modification of the Shay et al. technique reported in Gastroenterology, 26, 906 (1954). Male Sprague-Dawley rats (CFE, 180–220 g), in individual cages, are allowed access solely to a solution of 8% sucrose and 0.2% sodium chloride ad libitum for 48 hours prior to administration of the compound to be tested. One hour after administration of the compound, the rat is anesthetized with ether, the pylorus is exposed by a mid-line laparotomy and tied off with surgical thread, and the incision is closed with autoclips. Three hours later the rat is sacrificed by cervical dislocation. The incision is reopened, the esophagus is clamped at the cardiac sphincter, and the entire stomach is excised. The stomach is cut open and the contents are allowed to drain into a centrifuge tube. The mucosa is washed with 2 ml of saline and the wash is added to the contents. The stomach contents are centrifuged at 600 × gravity for 30 minutes, after which the supernatant is decanted, mixed with 10 ml of saline and titrated to pH 7 using 0.02N sodium hydroxide. The number of equivalents of sodium hydroxide used is a measure of the amount of acid produced. The less sodium hydroxide required, the less gastric acid produced, and the more effective the inhibition.

The compound to be tested is dissolved or suspended in an aqueous solution (containing 0.05% Tween 80) at appropriate concentrations so that oral or i.p. administration of 1 ml per 100 g of rat weight gives the proper dosage. For compounds that are insoluble in water, such may be tested by dissolving in either 0.01N hydrochloric acid (for i.p. dosing) or 3% lactic acid (for oral dosing). In each study, five animals are used per group, and the results compared to those obtained from experimental controls.

According to this test, for example, it has been found that at least 25% inhibition of gastric acid secretion, as compared with controls, are obtained at i.p. or oral doses of about 50 mg/kg of 2-(tetrahydrofuryl)perimidine.

It is well known that excessive secretion of gastric hydrochloric acid leads to unneeded peptic activity and endangers the mucous lining of the stomach. Indeed, prolonged action of excess hydrochloric acid can lead to ulceration of the gastric and duodenal mucosas. The use of gastric anti-secretory agents is thus desirable as an aid in the prevention and amelioration of distress occassioned by high concentrations of stomach acid.

In view of the anti-secretory activity of the subject compounds, there is provided herein a method of inhibiting gastric acid secretion which comprises internally administering to a gastric hyperacidic subject (man or animal) an effective gastric acid secretion inhibiting amount of 2-(tetrahydrofuryl)-perimidine, in base or acid addition salt form, preferably in admixture with a pharmaceutically acceptable carrier.

To prepare the pharmaceutical compositions of this invention, 2-(tetrahydrofuryl)perimidine or salt thereof is combined as the active ingredient in intimate admixture with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed, such as, for example, water, glycols, oils, alcohols, flavoring agents, preservatives, coloring agents and the like in the case of oral liquid preparations such as, for example, suspensions, elixirs and solutions; or carriers such as starches, sugars, diluents, granulating agents, lubricants, binders, disintegrating agents and the like in the case of oral solid preparations such as, for example, powders, capsules and tablets. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, from about 10 to about 500 mg of the active ingredient, and, preferably, from about 15 to about 250 mg.

The following examples are intended to illustrate, but not to limit, the scope of the present invention.

EXAMPLE I — Capsules 10,000 Hard gelatin capsules, each containing as the active ingredient (A.I.) 50 mg of 2-(tetrahydrofuryl)-perimidine, are prepared from the following formula formulation:

| | Grams |
|---|---|
| A.I. | 500 |
| Lactose | 750 |
| Starch | 250 |
| Talc | 250 |
| Calcium Stearate | 10 |

A uniform mixture of the active and supplementary ingredients is prepared and filled into two-piece hard gelatin capsules.

EXAMPLE II — Tablets 5,000 Compressed tablets, each containing as the active ingredient (A.I.) 10 mg of 2-(tetrahydrofuryl)-perimidine HCl, are prepared from the following formulation:

| | Grams |
|---|---|
| A.I. | 50 |
| Starch | 75 |
| Dibasic Calcium phosphate, hydrous | 500 |
| Calcium Stearate | 2.5 |

The finely powdered ingredients are mixed well and are granulated with 10% starch paste. The granulation is dried and compressed into tablets using starch as the disintegrant and calcium stearate as the lubricant.

EXAMPLE III — Injectable

The following formulation provides 1 liter of a parenteral suspension comprising 15 mg of 2-(tetrahydrofuryl)-perimidine as the active ingredient per milliliter:

| | Grams |
|---|---|
| A.I. | 15.0 |
| Polysorbate 80 | 2.0 |
| Sodium chloride | 9.0 |
| Sodium Carboxymethyl cellulose | 10.0 |
| Methyl paraben | 1.8 |
| Propyl paraben | 0.2 |
| Water for Injection, U.S.P., | q.s. ad |

Dissolve the parabens, sodium chloride, and carboxymethyl cellulose in one-half the total volume of water by heating to 95°C to obtain a clear solution. Filter and autoclave. Dissolve the polysorbate in one-third the total volume of water. Filter and autoclave this second solution. Add sterile A.I. to the second solution and pass it through a sterile colloid mill. To the resulting suspension add the first solution with uniform stirring. Q.s. with sterilized water and stir while filling into sterile vials.

EXAMPLE IV — Oral Suspension

The following formulation provides 5 liters of an oral suspension comprising 100 mg of 2-(tetrahydrofuryl)-perimidine as the active ingredient per teaspoonful (5 mls):

| | Grams |
|---|---|
| A.I. | 100.0 |
| Sucrose | 300.0 |
| Dioctyl sodium sulfosuccinate | 0.5 |
| Bentonite | 22.5 |
| Methyl paraben | 7.5 |
| Propyl paraben | 1.5 |
| Antifoam A.F. Emulsion | 0.15 |
| Propylene glycol | 52.0 |
| FD&C Yellow No. 5 | 0.1 |
| Sodium cyclamate | 50.0 |
| Sodium saccharin | 5.0 |
| Orange flavor | 7.5 |
| Filtered purified water, q.s. ad | 5 liters |

Dissolve the parabens in the propylene glycol and add this solution to a solution of the sodium cyclamate, sodium saccharin and sucrose in half the water. Suspend the bentonite in hot (about 85°C) water and stir for 60 minutes. Add the bentonite solution to the former solution. Dissolve the sulfosuccinate in some water and suspend the A.I. in the resulting solution. Add the Antifoam A.F. Emulsion which has been diluted to a lotion consistency with a minimum amount of water and mix well. Add the latter suspension of A.I. to the former mixture and mix well. Add the FD&C Yellow No. 5 dissolved in a small amount of water. Add the orange flavor, q.s. to volume with water, and stir to a homogeneous mixture. Pass the mixture through a colloid mill and fill into suitable containers.

EXAMPLE V 10,000 Hard gelatin capsules, each containing as the active ingredient (A.I.) 400 mg of 2(3H)-perimidylidene-2-propanone, are prepared from the following formulation:

| | Grams |
|---|---|
| A.I. | 4000 |
| Lactose | 750 |
| Starch | 250 |
| Talc | 250 |
| Calcium Stearate | 10 |

A uniform mixture of the active and supplementary ingredients is prepared and filled into two-piece hard gelatin capsules.

The foregoing pharmaceutical compositions are examples of unit dosages suitable for internal administration to man or other warm blooded animals for gastric antisecretory purposes.

The compound of formula (I) may be converted to the corresponding therapeutically active non-toxic acid addition salt form by reaction with an appropriate inorganic acid, such as, for example, hydrochloric, hydrobromic, hydriodic, sulfuric, phosphoric, nitric and the like acids, or with an appropriate organic acid, such as, for example, acetic, propionic, glycolic, lactic, oxalic, malonic, sulfamic, p-toluenesulfonic and the like acids. In turn, the acid addition salts may be converted to the corresponding free base form by conventional treatment with suitable alkali.

What is claimed is:

1. A method of inhibiting gastric acid secretion in a gastric hyperacidic subject which comprises internally administering thereto an effective gastric acid secretion inhibiting amount of a member selected from the group consisting of 2-(tetrahydrofuryl)-perimidine and a pharmaceutically acceptable acid addition salt thereof.

2. A method of inhibiting gastric acid secretion in a gastric hyperacidic subject which comprises internally administering thereto a pharmaceutical composition in dosage unit form comprising per dosage unit from about 10 to about 500 mg of a member selected from the group consisting of 2-(tetrahydrofuryl)perimidine and a pharmaceutically acceptable acid addition salt thereof in admixture with a pharmaceutically acceptable carrier.

* * * * *

UNITED STATES PATENT OFFICE
CERTIFICATE OF CORRECTION

Patent No. 3,956,496   Dated May 11, 1976

Inventor(s) Russell J. Taylor, Jr.

It is certified that error appears in the above-identified patent and that said Letters Patent are hereby corrected as shown below:

Column 2, line 67, delete "formula"

Column 3, line 44, in Example III, in the chart, under "Grams" insert -- 1 liter --.

Signed and Sealed this

Fifteenth Day of March 1977

[SEAL]

Attest:

RUTH C. MASON
*Attesting Officer*

C. MARSHALL DANN
*Commissioner of Patents and Trademarks*